US012453385B2

(12) United States Patent
Eom et al.

(10) Patent No.: US 12,453,385 B2
(45) Date of Patent: Oct. 28, 2025

(54) WOMEN'S TOP FOR BREAST SHAPING AND THORACIC SPINE CORRECTION

(71) Applicant: DODREAMCREATIVE CO., LTD., Jongno-Gu Seoul (KR)

(72) Inventors: Tae Ho Eom, Songpa-Gu Seoul (KR); Seung Ah Lee, Songpa-Gu Seoul (KR)

(*) Notice: Subject to any disclaimer, the term of this patent is extended or adjusted under 35 U.S.C. 154(b) by 5 days.

(21) Appl. No.: 18/034,527

(22) PCT Filed: Oct. 29, 2020

(86) PCT No.: PCT/KR2020/014935
§ 371 (c)(1),
(2) Date: Apr. 28, 2023

(87) PCT Pub. No.: WO2022/092356
PCT Pub. Date: May 5, 2022

(65) Prior Publication Data
US 2024/0358094 A1 Oct. 31, 2024

(51) Int. Cl.
*A41C 3/00* (2006.01)
*A61F 5/02* (2006.01)
*A61F 5/03* (2006.01)

(52) U.S. Cl.
CPC ............ *A41C 3/0064* (2013.01); *A61F 5/024* (2013.01); *A61F 5/03* (2013.01)

(58) Field of Classification Search
CPC ........ A41D 13/0015; A41C 3/03; A41C 3/02; A61F 5/026; A61F 5/00
USPC ........................................................... 450/30
See application file for complete search history.

(56) References Cited

U.S. PATENT DOCUMENTS 3,008,468 A * 11/1961 Kravadze ................. A41C 3/00 450/86
3,856,004 A * 12/1974 Cox .................... A61F 5/05808 2/45
5,135,470 A * 8/1992 Reeves ................... A61F 5/026 D29/101.1

(Continued)

FOREIGN PATENT DOCUMENTS

CN 110623321 A 12/2019
JP H01107317 U 11/2003

(Continued)

OTHER PUBLICATIONS

Office Action for Chinese Patent Application dated Nov. 15, 2024.

(Continued)

*Primary Examiner* — Timothy K Trieu
(74) *Attorney, Agent, or Firm* — Steven Scott Lloyd

(57) ABSTRACT

This women's top for breast shaping and thoracic spine correction comprises: a main body covering the upper body of a user; a first band disposed on one side of the main body; a second band which is disposed on the other side of the main body and at least a part of which is connected, on the front of the main body, to the first band; and a lumbar vertebra support disposed on the back of the main body, wherein the lumbar vertebra support includes a first section overlapping the first band, a second section overlapping the second band, and a third section extending downward from the first and second sections.

12 Claims, 3 Drawing Sheets

(56) References Cited

U.S. PATENT DOCUMENTS

| | | | | |
|---|---|---|---|---|
| 7,871,388 | B2 * | 1/2011 | Brown .................. | A61F 5/3746 602/19 |
| 2005/0197607 | A1 * | 9/2005 | Brown ................. | A61N 1/0484 602/19 |
| 2010/0256717 | A1 * | 10/2010 | Brown ................. | A41D 31/185 607/115 |
| 2012/0059297 | A1 | 3/2012 | Newkirk | |
| 2012/0316483 | A1 | 12/2012 | Waeger | |
| 2013/0296756 | A1 * | 11/2013 | Troncoso .................. | A61F 5/02 602/19 |
| 2015/0094634 | A1 | 4/2015 | Waeger | |
| 2016/0278963 | A1 | 9/2016 | Webster et al. | |
| 2017/0354530 | A1 | 12/2017 | Shagdar | |
| 2019/0029866 | A1 | 1/2019 | Stier et al. | |

FOREIGN PATENT DOCUMENTS

| | | | |
|---|---|---|---|
| JP | 3115670 | A | 11/2005 |
| JP | 2007138335 | A | 6/2007 |
| JP | 2013085696 | A | 5/2013 |
| KR | 20-2013-0004794 | U | 8/2013 |
| KR | 20190041021 | A | 4/2019 |

OTHER PUBLICATIONS

Notice of Allowance for Japanese Patent Application JPH01107317U dated Sep. 11, 2024.

* cited by examiner

WOMEN'S TOP FOR BREAST SHAPING AND THORACIC SPINE CORRECTION

CROSS-REFERENCE TO RELATED APPLICATION(S)

The present application derives priority from PCT patent application No. PCT/KR2020/014935 filed 29 Oct. 2020.

FIELD

The present embodiment relates to a women's top for breast shaping and thoracic spine correction.

BACKGROUND

In general, women's brassiere underwear is clothing worn on the inside the garment, and other functions other than the use of clothing or beauty cannot be expected. In particular, the effect of correcting the backbone or spine could not be expected.

Modern people are engaged in various jobs, and most of their tasks are to organize or process documents for a long time with their shoulders bent in front of their desks, so if they do these tasks for a long time, problems such as bending their upper body forward and bending their spine can occur.

In order to prevent bending of the spine due to forward bending of the upper body, it is necessary to always maintain a correct posture while working and exercise regularly, but it is difficult for busy modern people.

Therefore, various types of compression clothing, correction underwear, and correction devices are being developed to prevent the upper body from bending forward, but there is a problem in that satisfactory effects are not obtained.

SUMMARY

The problem that the present embodiment is trying to solve is to provide a women's top for upper body correction that supports the thoracic spine and straightens the back while at the same time pulling the breast in the opposite direction of gravity and enhancing the volume with a beautiful triangular line which is a differentiated female body characteristic from men.

A women's top for breast shaping and thoracic spine correction according to the present embodiment comprises: a main body covering the upper body of a user; a first band being disposed on one side of the main body; a second band being disposed on the other side of the main body and at least a part of which is connected, on the front of the main body, to the first band; and a lumbar vertebra support being disposed on the back of the main body, wherein the lumbar vertebra support includes a first section being overlapped with the first band, a second section being overlapped with the second band, and a third section being extended downward from the first and second sections.

In addition, each of the first and second bands includes first and second round parts being disposed on the front surface of the main body, and one end portion of the first round part may be coupled with one end portion of the second round part.

In addition, the first band may include a first portion being extended upward from the other end portion of the first round part, and the second band may include a first portion being extended upward from the other end portion of the second round part.

In addition, the first band includes a second portion being extended from the first portion of the first band to the rear surface of the main body, the second band includes a second portion being extended from the first portion of the second band to the rear surface of the body, and the second portion of the first band and the second portion of the second band may be intersected at the rear surface of the main body.

In addition, the first band includes a third portion being extended from the second portion of the first band to the front surface of the main body; the second band includes a third portion being extended from the second portion of the second band to the front surface of the body; the third portion of the first band and the third portion of the second band are disposed below the first round part and the second round part; and the third portion of the first band and the third portion of the second band may be coupled to each other and fixed to the main body.

In addition, the third portion of the first band may be pulled in a first direction, and the third portion of the second band may be pulled in a second direction being intersected with the first direction.

In addition, when the third portion of the first band is pulled in the first direction and the third portion of the second band is pulled in the second direction, the first round part and the second round part are may be pulled in a third direction.

In addition, it may be greater than the degree to which the third region of the lumbar vertebra support is deformed.

In addition, the maximum width in a horizontal direction between the first section and the second section of the lumbar vertebra support may be greater than the width of the third section of the lumbar vertebra support in a corresponding direction.

In addition, the shortest width in the horizontal direction between the first section and the second section of the lumbar vertebra support may be greater than a width of the third section of the lumbar vertebra support in a corresponding direction.

Through present embodiment, it is possible to provide a female top for upper body correction that supports the thoracic vertebrae and straightens the back while pulling the breast in the opposite direction of gravity and enhancing the volume with a beautiful triangular line, which is a characteristic of the female body differentiated from that of men.

DETAILED DESCRIPTION

Hereinafter, preferred embodiments of the present invention will be described in detail with reference to the accompanying drawings. Advantages and features of the present invention, and methods of achieving them, will become clear with reference to the embodiments described below in detail in conjunction with the accompanying drawings. However, the present invention is not limited to the embodiments disclosed below and may be implemented in various different forms, only the present embodiments make the disclosure of the present invention complete, it is provided to completely inform those skilled in the art of the scope of the invention to which the present invention belongs, and the present invention is only defined by the scope of the claims. Same reference numbers designate same components throughout the specification.

Unless otherwise defined, all terms (including technical and scientific terms) used in this specification may be used in a meaning commonly understood by those of ordinary skill in the art to which the present invention belongs. In addition, terms defined in commonly used dictionaries are not interpreted ideally or excessively unless explicitly specifically defined.

In addition, the terms used in the present specification are for describing the embodiments and are not intended to limit the present invention. In the present specification, singular forms also include plural forms unless specifically stated otherwise in a phrase. The terms “comprises” and/or “comprising” as used in the specification do not exclude the presence or addition of one or more other components, steps and/or operations in addition to the components, steps and/or operations mentioned. And “and/or” includes each and every combination of one or more of the mentioned items.

In addition, terms such as first, second, A, B, (a), and (b) may be used in describing components of an embodiment of the present invention. These terms are only used to distinguish the component from other components, and the nature, order, or order of the corresponding component is not limited by the term. When a component is described as being ‘connected’, ‘coupled’ or ‘interconnected’ to another component, the component may be directly connected, coupled or interconnected to the other component, but not between the component and the . . . other component, but it should be understood that another component may be ‘connected’, ‘coupled’ or ‘interconnected’ between the component and the other component.

An ‘optical axis direction’ used below is defined as an optical axis direction of a lens coupled to a lens driving device. Meanwhile, the ‘optical axis direction’ may correspond to ‘up and down directions’ and ‘z-axis directions’.

Hereinafter, the present embodiment will be described in more detail according to the accompanying drawings.

Figure 1:
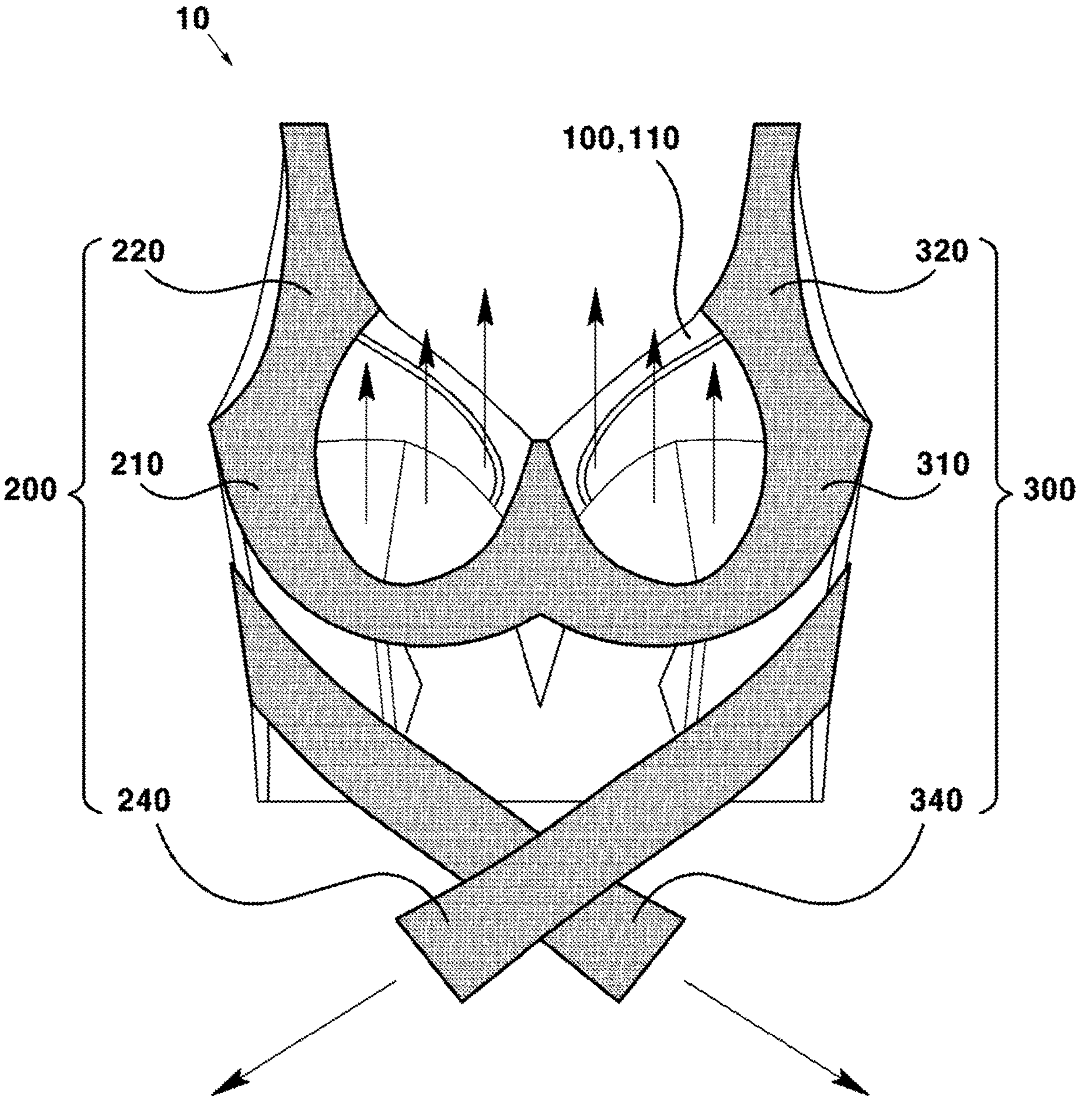
FIG. 1 is a front view of a female top for breast correction and thoracic spine correction according to present embodiment.
Figure 2:
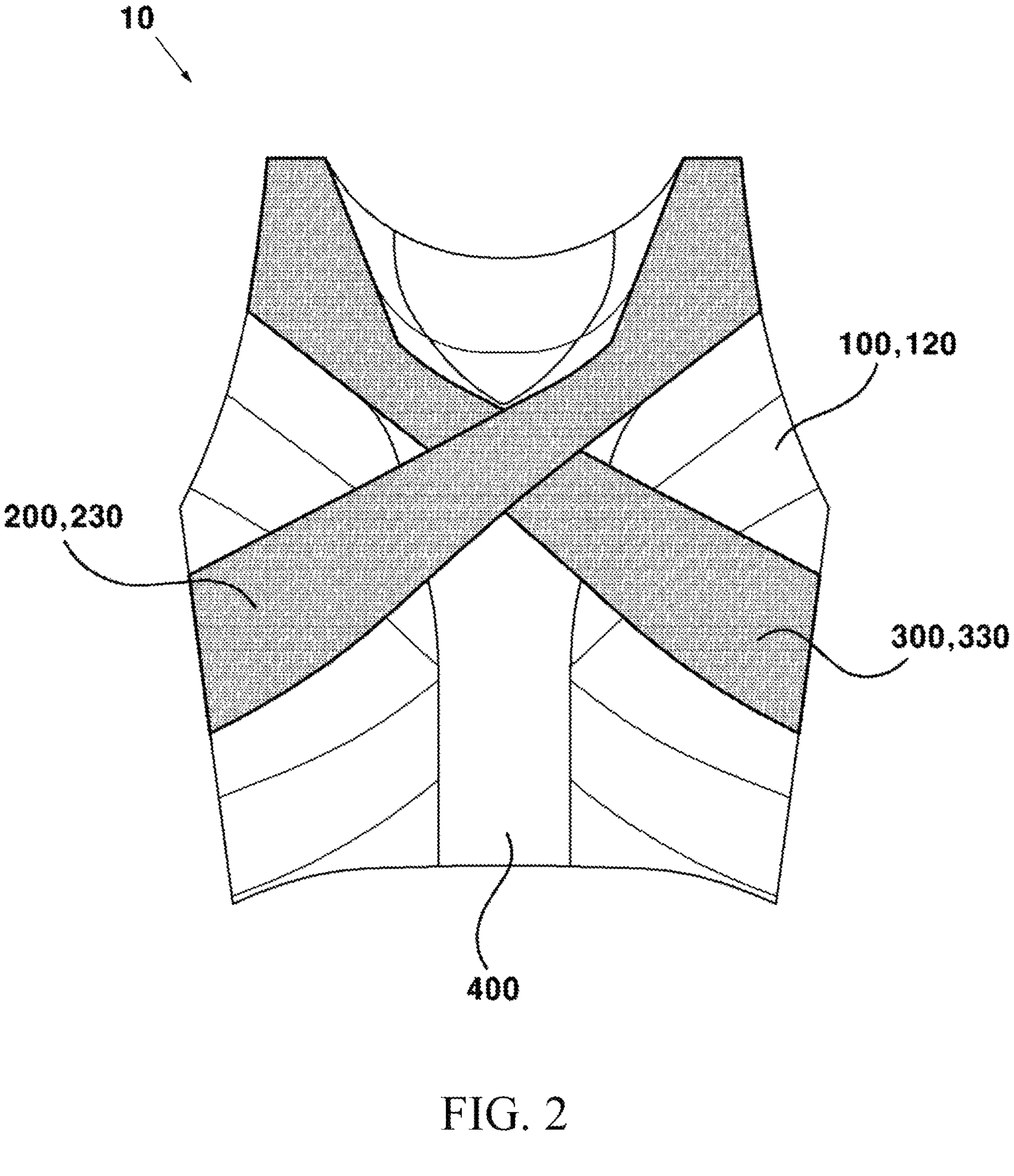
FIG. 2 is a rear view of a female top for breast correction and thoracic spine correction according to the present embodiment.
Figure 3:
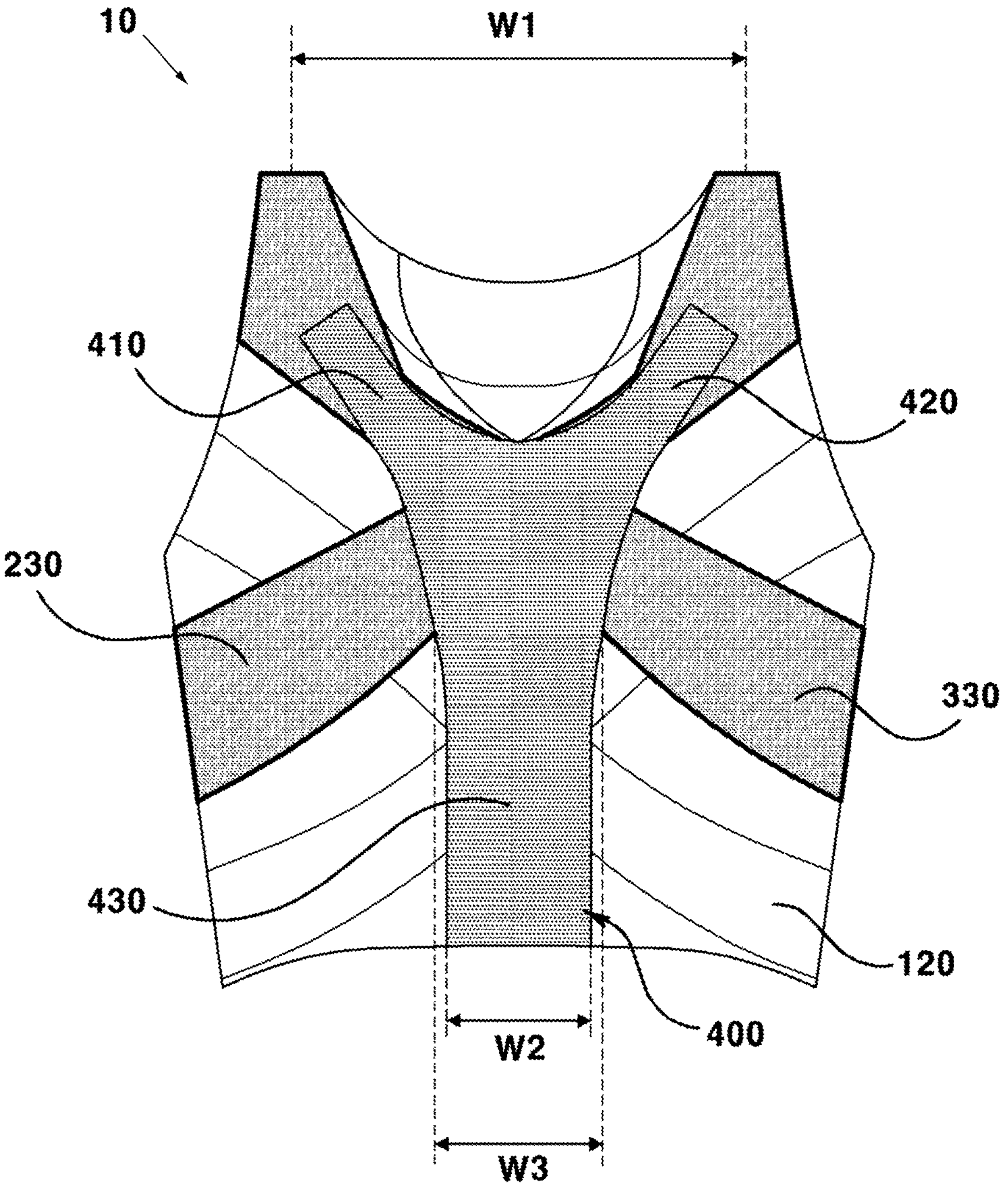
FIG. 3 is a rear view of a female top for breast correction and thoracic spine correction according to the present embodiment.

FIG. 1 is a front view of a female top for breast correction and thoracic spine correction according to present embodiment. FIG. 2 is a rear view of a female top for breast correction and thoracic spine correction according to the present embodiment. FIG. 3 is a rear view of a female top for breast correction and thoracic spine correction according to the present embodiment.

Referring to FIGS. 1 to 3, women’s top 10 for breast correction and thoracic spine correction according to the present embodiment may include a main body 100, a first band 200, a second band 300, and a lumbar vertebra support 400, but it may be implemented except for some of these configurations, and other additional configurations are not excluded.

The women’s top 10 for breast correction and thoracic spine correction may include a main body 100. The main body 100 may cover the user’s upper body. The main body 100 may surround the user’s shoulder, breast, and back. At least a portion of the main body 100 may be formed as a corset surface. The body 100 may include a wire. The main body 100 may be formed of an elastic material. The main body 100 may comprise a front surface 110 and a rear surface 120. The front surface 110 may be a direction directing forward when the user wears the women’s top 10 for breast correction and thoracic spine correction. The rear surface 120 may be a direction directing rearward when the user wears the women’s top 10 for breast correction and thoracic spine correction. The rear surface 120 may be disposed at an opposite side of the front surface 110. The front surface 120 and the rear surface 120 may be integrally formed.

The women’s top 10 for breast correction and thoracic spine correction may include a first band 200. The first band 200 may be disposed in the main body 100. The first band 200 may be disposed on the front surface 110 of the main body 100. The first band 200 may be disposed on the rear surface 120 of the main body 100.

The first band 200 may be formed of only an elastic material. The first band 200 may be formed only of inelastic material. The first band 200 may be formed of an elastic material and an inelastic material. Specifically, a portion of the first band 200 is formed of an elastic material, and the remaining portion may be formed of an inelastic material.

The first band 200 may include a first round part 210. The first round part 210 may be disposed on the front surface 110 of the main body 100. One end portion of the first round part 210 may be coupled with one end portion of a second round part 310, which will be described later. The first round part 210 may be placed below the user’s breast when the user wears the women’s top 10 for breast correction and thoracic spine correction. The user’s breast of the first round part 210 can be raised upward from below.

The first band 200 may include a first portion 220. The first portion 220 of the first band 200 may be extended upward from the other end portion of the first round part 210.

The first band 200 may include a second portion 230. The second portion 230 of the first band 200 may be extended from the first portion 220 of the first band 200 to the rear surface 120 of the main body 100. The second portion 230 of the first band 200 may be intersected with a fifth portion 330 of the second band 300, which will be described later, at the rear surface 120 of the main body 100. At this time, the second portion 230 of the first band 200 may be intersected with the fifth portion 330 of the second band 300 in the shape of a letter ‘X’. At least a portion of the second portion 230 of the first band 200 may be overlapped with the fifth portion 330 of the second band 300.

The first band 200 may include a third portion 240. The third portion 240 of the first band 200 may be extended from the second portion 230 of the first band 200 to the front surface 110 of the main body 100. The third portion 240 of the first band 200 may be disposed below the first round part 210. At least a portion of the third portion 240 of the first band 200 may be disposed below a second round part 310, which will be described later. The third portion 240 of the first band 200 may be coupled with a sixth portion 340 of the second band 300, which will be described later. At this time, the first and second bands 200 and 300 may be fixed to the main body 100.

The women’s top 10 for breast correction and thoracic spine correction may include a second band 300. The second band 300 may be disposed in the main body 100. The second band 300 may be disposed on the front surface 110 of the main body 100. The second band 300 may be disposed on the rear surface 120 of the main body 100. The second band 300 may be coupled with the first band 200.

The second band 300 may be formed only of an elastic material. The second band 300 may be formed only of an inelastic material. The second band 300 may be formed of an elastic material and an inelastic material. Specifically, a portion of the second band 300 may be formed of an elastic material, and the remaining portion may be formed of an inelastic material.

The second band 300 may include a second round part 310. The second round part 310 may be disposed on the front surface 110 of the main body 100. One end portion of the second round part 310 may be coupled with one end portion of the first round part 210. The second round part 310 may be disposed below the user's breast when the user wears the women's top 10 for breast correction and thoracic spine correction. The user's breast of the third round part 310 can be raised upward from below.

The second band 300 may include a fourth portion 320. The fourth portion 320 of the second band 300 may be extended upward from the other end portion of the second round part 310.

The second band 300 may include a fifth portion 330. The fifth portion 330 of the second band 300 may be extended from the fourth portion 320 of the second band 300 to the rear surface 120 of the main body 100. The fifth portion 330 of the second band 300 may be intersected with the second portion 230 of the first band 200 at the rear surface 120 of the main body 100. At this time, the fifth portion 330 of the second band 300 may be intersected with the second portion 230 of the first band 200 in the shape of a letter 'X'. At least a portion of the fifth portion 330 of the second band 300 may be overlapped with the second portion 230 of the first band 200.

The second band 300 may include a sixth portion 340. The sixth portion 340 of the second band 300 may be extended from the fifth portion 330 of the second band 300 to the front surface 110 of the main body 100. The sixth portion 340 of the second band 300 may be disposed below the second round part 310. At least a portion of the sixth portion 340 of the second band 300 may be disposed below the first round part 210. The sixth portion 340 of the second band 300 may be coupled with the third portion 240 of the first band 200. At this time, the first and second bands 200 and 300 may be fixed to the main body 100.

The third portion 240 of the first band 200 may be pulled in a first direction. The sixth portion 340 of the second band 300 may be pulled in a second direction. The first direction may be a direction intersecting the second direction. In this case, the intersection angle of the first direction and the second direction may be an obtuse angle. The intersection angle between the first direction and the second direction may be 120 degrees.

When the third portion 240 of the first band 200 is pulled in a first direction and the sixth portion 340 of the second band 300 is pulled in a second direction, the first round part 210 may be pulled in a third direction. The third direction may be a direction being intersected with the first direction and the second direction. The intersection angle between the third direction and the first direction may be an obtuse angle. The intersection angle between the third direction and the second direction may be an obtuse angle. An intersection angle being formed by each of the first to third directions may be 120 degrees. Through this, the force pulling the third portion 240 of the first band 200 and the sixth portion 340 of the second band 300 can be evenly distributed. In this case, the tensile force may be evenly distributed throughout the first and second bands 200 and 300. The third direction may be an upward direction of the first and second round parts 210 and 310. Through this, the breast can be pulled upward so that it does not sag.

The third portion 240 of the first band 200 and the sixth portion 340 of the second band 300 may be coupled to each other at the front surface 110 of the main body 100. As a coupling method, there may be a ribbon type, a strap type, a hook type, a belt type, a Velcro type, a button type, and the like.

The third portion 240 of the first band 200 and the sixth portion 340 of the second band 300 may be coupled in a ribbon type. The third portion 240 of the first band 200 and the sixth portion 340 of the second band 300 can be coupled by being tied in various shapes such as ribbons and ties on the front surface 110 of the main body 100. At this time, the user can adjust the tying strength to adjust the correction effect according to the user's body. Through this, the first and second round parts 210 and 310 can lift the weight of the breast from below the breast by lever principle. At the same time, the lumbar vertebra support 400, which will be described later, is pressurized to maintain a correct posture.

The third portion 240 of the first band 200 and the sixth portion 340 of the second band 300 may be coupled in a strap type. The third portion 240 of the first band 200 may include a length adjusting member. The length adjusting member may include a hole. The length adjusting member may include first and second holes being spaced apart from each other. The second hole of the length adjusting member may be disposed below the first hole of the length adjusting member. A first portion 240 of the first band 200 may penetrate through and be fixed to the first hole of the length adjusting member. The sixth portion 340 of the second band 300 may penetrate through the first hole of the length adjusting member of the third portion 240 of the first band 200. The sixth portion 340 of the second band 300 penetrating through the first hole of the length adjusting member may penetrate through the second hole of the length adjusting member. In this case, the size of the sixth portion 340 of the second band 300 may be adjustable by penetrating through the first and second holes of the length adjusting member. Through this, the lengths of the first and second bands 200 and 300 can be adjusted to be suitable to the user's body characteristics. In addition, the lengths of the first and second bands 200 and 300 may be adjusted according to areas or strengths requiring correction. Through this, the first and second round parts 210 and 310 can lift the weight of the breast below the breast by lever principle. At the same time, a lumbar vertebra support 400, which will be described later, is pressurized to maintain a correct posture.

The third portion 240 of the first band 200 and the sixth portion 340 of the second band 300 may be coupled in a hook type. Specifically, the third portion 240 of the first band 200 may include a ring in which a hole is formed. The sixth portion 340 of the second band 300 may include a hook. The hook of the sixth portion 340 of the second band 300 may be coupled to the hook of the third portion 240 of the first band 200. However, it is not limited thereto, and the third portion 240 of the first band 200 may include a hook, and the sixth portion 340 of the second band 300 may include a hole. The number of holes in the third portion 240 of the first band 200 may be plural. The hooks of the sixth portion 340 of the second band 300 may be plural. Through this, it is possible to adjust the user's body size, the user's body characteristics, the body part to be corrected, and the intensity of correction. Through this, the first and second round parts 210 and 310 can lift the weight of the breast below the breast by lever principle. At the same time, the lumbar vertebra support 400, which will be described later, is pressurized to maintain a correct posture.

The third portion 240 of the first band 200 and the sixth portion 340 of the second band 300 may be coupled in a belt type. Specifically, the third portion 240 of the first band 200 may include a buckle. The buckle may include a pin. A plurality of holes may be formed in the sixth portion 340 of the second band 300. The sixth portion 340 of the second band 300 may penetrate through the buckle of the third portion 240 of the first band 200. At this time, the pin of the buckle may be inserted into and fixed to any one of the plurality of holes of the sixth portion 340 of the second band 300. In this case, the pin of the buckle can be inserted into the hole by adjusting the length of the sixth portion 340 of the second band 300 in consideration of the user's body characteristics, body size, desired region to be corrected, and intensity of correction. However, it is not limited thereto, and a plurality of holes are formed in the third portion 240 of the first band 200, and the sixth portion 340 of the second band 300 may include a buckle.

The third portion 240 of the first band 200 and the sixth portion 340 of the second band 300 may be coupled in a Velcro type. Specifically, the third portion 240 of the first band 200 may include a first adhesive member. The sixth portion 340 of the second band 300 may include a second adhesive member. Through this, the first adhesive member and the second adhesive member may be coupled to each other. The first adhesive member may be disposed on the entire third portion 240 of the first band 200. The second adhesive member may be disposed on the entire sixth portion 340 of the second band 300. Through this, the length and size of the first and second bands 200 and 300 can be adjusted in consideration of the user's body characteristics, body size, region to be corrected, and intensity of correction. Through this, the first and second round parts 210 and 310 can lift the weight of the breast below the breast by lever principle. At the same time, the lumbar vertebra support 400, which will be described later, is pressurized to maintain a correct posture.

The third portion 240 of the first band 200 and the sixth portion 340 of the second band 300 may be coupled in a button type. At this time, the button may mean a snap button or a click button. Specifically, a female button for a snap button is disposed in the third portion 240 of the first band 200, and a male button may be disposed in the sixth portion 340 of the second band 300. In addition, a male button for a snap button may be disposed in the third portion 240 of the first band 200, and a female button for a snap button may be disposed in the sixth portion 340 of the second band 300. A plurality of female buttons for snap buttons and male buttons for snap buttons may be provided. Through this, it is possible to adjust the length of the first and second bands 200 and 300 according to the user's body characteristics, size, and body part to be corrected. The first band 200 and the second band 300 may be fixed as the female button for snap button and the male button for snap button are coupled to each other.

The third portion 240 of the first band 200 and the sixth portion 340 of the second band 300 are extended from the rear surface 120 of the main body 100 to the front surface 100, thereby surrounding the abdominal area. In this case, the lengths of the third portions 240 and 340 in a vertical direction may be increased. In this case, upper ends of the second portions 240 and 340 may be overlapped with lower ends of the first and second round parts 210 and 310.

The women's top 10 for breast correction and thoracic spine correction may include a lumbar vertebra support 400. The lumbar vertebra support 400 may be disposed on the main body 100. The lumbar vertebra support 400 may be disposed on the rear surface 120 of the main body 100. The lumbar vertebra support 400 may be disposed between the first and second bands 200 and 300 and the main body 100. Or, the lumbar vertebra support 400 may be disposed between the outer and inner surfaces of the rear surface 120 of the main body 100. FIG. 3 is a drawing illustrating the lumbar vertebra support 400 at an outer side of the first and second bands 200 and 300 to confirm the arrangement relationship between the lumbar vertebra support 400 and the first and second bands 200 and 300.

The lumbar vertebra support 400 may include a first section 410. The first section 410 may be overlapped with the first band 200. The first section 410 may be overlapped with at least a portion of the second portion 230 of the first band 200. The lumbar vertebra support 400 may include a second section 420. The second section 420 may be overlapped with the second band 300. The second section 420 may be overlapped with at least a portion of the fifth portion 330 of the second band 200. The lumbar vertebra support 400 may include a third section 430. The third section 430 may be extended downward from the first and second sections 410 and 420.

The lumbar vertebra support 400 may be formed of a silicon material. However, it is not limited thereto, and may be formed of an elastic material. The lumbar vertebra support 400 may be pressed in a direction directing from the rear surface 120 of the main body 100 to the front surface 110 of the main body 100 by the first and second bands 200 and 300. The lumbar vertebra support 400 may be deformed by the first and second bands 200 and 300. The degree of deformation of the first and second sections 410 and 420 of the lumbar vertebra support 400 may be greater than the degree of deformation of the third section 430 of the lumbar vertebra support 400. Through this, the user's spine, back, and shoulders can be stretched.

The lumbar vertebra support 400 may be formed in the shape of a letter 'Y'. The lumbar vertebra support 400 may be disposed at the central portion of the main body 100. The lumbar vertebra support 400 may be formed symmetrically about the central portion of the main body 100. The lumbar vertebra support 400 may have a narrower width in the horizontal direction as it travels downward from above. Specifically, the maximum width W1 in the horizontal direction between the first section 410 and the second section 420 of the lumbar vertebra support 400 may be formed to be larger than the width W2 in the corresponding direction of the third section 430 of the lumbar vertebra support 400. The shortest width W3 between the first section 410 and the second section 420 of the lumbar vertebra support 400 in the horizontal direction may be formed to be larger than the width W2 in the corresponding direction of the third section 430 of the lumbar vertebra support 400. Through this, the user's thoracic vertebrae and cervical vertebrae may be intensively pressed to induce a correct posture.

Although the embodiment of the present invention has been described above with reference to the accompanying drawings, those of ordinary skill in the art to which the present invention belongs will understand that the present invention may be embodied in other specific forms without changing the technical spirit or essential features thereof. Therefore, it should be understood that the embodiments described above are illustrative in all respects and not restrictive.

| [Description of the Symbols] | |
| --- | --- |
| 100: main body | 200: first band |
| 300: second band | 400: lumbar vertebra support |

The invention claimed is:

1. A female upper garment for breast shaping and thoracic spine correction comprising: a main body surrounding the upper body of a user and having a front surface and a rear surface; a first band being disposed on one side of the main body;

a second band being disposed on the other side of the main body, the second band being connected to the first band on the front surface of the main body; and a lumbar vertebra support being disposed on the rear surface of the main body, wherein the lumbar vertebra support includes a first section overlapped with the first band, a second section overlapped with the second band, and a third section extended downward from the first and second sections and, wherein the first band includes a first round part disposed on the front surface of the main body and disposed below one breast of a user, wherein the second band includes a second round part disposed on the front surface of the main body and disposed below the user's other breast, and wherein one end of the first round part and one end of the second round part are interconnected; wherein a maximum horizontal distance between the first section and the second section of the lumbar vertebra support is greater than the width of the third section of the lumbar vertebra support.

2. The female upper garment for breast shaping and thoracic spine correction according to claim 1, wherein the first band includes a first portion extended upward from another end of the first round part, and wherein the second band includes a fourth portion extended upward from another end of the second round part.

3. The female upper garment for breast shaping and thoracic spine correction according to claim 2, wherein the first band includes a second portion extended from the first portion to the rear surface of the main body, wherein the second band includes a fifth portion extended from the fourth portion to the rear surface of the main body, and wherein the second portion and the fifth portion are intersected at the rear surface of the main body.

4. The female upper garment for breast shaping and thoracic spine correction according to claim 3, wherein the first section of the lumbar vertebra support is overlapped with the second portion of the first band, and wherein the second section of the lumbar vertebra support is overlapped with the fifth portion of the second band.

5. The female upper garment for breast shaping and thoracic spine correction according to claim 3, wherein the first band includes a third portion extended from the second portion to the front surface of the main body, wherein the second band includes a sixth portion extended again from the fifth portion to the front surface of the main body, wherein the third portion and the sixth portion are disposed below the first round part and the second round part, and wherein the third portion and the sixth portion are coupled to each other and fixed at the front surface of the main body.

6. The female upper garment for breast shaping and thoracic spine correction according to claim 5, wherein the third portion is configured to be pulled in a first direction, and wherein the sixth portion is configured to be pulled in a second direction intersecting the first direction.

7. The female upper garment for breast shaping and thoracic spine correction according to claim 6, wherein the first round part and the second round part are pulled in a third direction when the third portion is pulled in the first direction and the sixth portion is pulled in the second direction.

8. The female upper garment for breast shaping and thoracic spine correction according to claim 7, wherein an angle formed by the first direction and the second direction, an angle formed by the second direction and the third direction, and an angle formed by the first direction and the third direction are 120 degrees respectively.

9. The female upper garment for breast shaping and thoracic spine correction according to claim 7, wherein the third direction is upward from the first and second round parts.

10. The female upper garment for breast shaping and thoracic spine correction according to claim 1, wherein the lumbar vertebra support is formed of a silicon material, and wherein the lumbar vertebra support is deformed by the deformation of the first and second bands.

11. The female upper garment for breast shaping and thoracic spine correction according to claim 10, wherein the first and second sections and of the lumbar vertebra support are deformed more than the third section of the lumbar vertebra support.

12. The female upper garment for breast shaping and thoracic spine correction according to claim 1, wherein a shortest distance in the horizontal direction between the first section and the second section of the lumbar vertebra support is greater than the width in the corresponding direction of the third section of the lumbar vertebra support.

* * * * *